United States Patent [19]

Pirl

[11] Patent Number: 5,025,215

[45] Date of Patent: Jun. 18, 1991

[54] SUPPORT EQUIPMENT FOR A COMBINATION EDDY CURRENT AND ULTRASONIC TESTING PROBE FOR INSPECTION OF STEAM GENERATOR TUBING

[75] Inventor: William E. Pirl, Levelgreen, Pa.

[73] Assignee: Westinghouse Electric Corp., Pittsburgh, Pa.

[21] Appl. No.: 394,702

[22] Filed: Aug. 16, 1989

[51] Int. Cl.$^5$ .................. G01N 27/82; G01N 29/06; G21C 17/017

[52] U.S. Cl. ..................... 324/220; 73/623; 73/866.5; 165/11.2; 324/226; 376/245; 414/590

[58] Field of Search ............... 324/219–221, 324/226, 227; 73/622, 623, 633, 634, 866.5; 165/11.2; 198/722–724; 376/245, 249, 254; 74/22 R; 414/749, 750, 787, 589, 590; 33/544.1

[56] References Cited

U.S. PATENT DOCUMENTS

| | | | |
|---|---|---|---|
| 3,831,084 | 8/1974 | Scalese et al. | |
| 4,303,884 | 12/1981 | Malick | 324/220 |
| 4,389,611 | 6/1983 | Pigeon et al. | 324/220 |
| 4,438,399 | 3/1984 | Schnabl et al. | 324/220 |
| 4,449,411 | 5/1984 | Suhr et al. | 73/643 |
| 4,494,907 | 1/1985 | Coussau et al. | 324/220 X |
| 4,505,323 | 3/1985 | de la Pintiere et al. | 165/11.2 |
| 4,625,165 | 11/1986 | Rothstein | 324/220 |
| 4,668,912 | 5/1987 | Junker | 324/220 |
| 4,710,710 | 12/1987 | Flora et al. | 324/220 |
| 4,727,321 | 2/1988 | Huschelrath | 324/226 |
| 4,769,598 | 9/1988 | Krieg et al. | 324/219 |
| 4,770,053 | 9/1988 | Broderick et al. | 165/11.2 X |

Primary Examiner—Gerard R. Strecker

[57] ABSTRACT

A system for helically driving an inspection probe within a tube of a nuclear steam generator is provided, wherein the system is particularly useful in driving a combination eddy-current and ultrasonic probe. The system generally includes a head assembly insertable with the tube for inspection, a drive frame assembly to be located external of the steam generator, and a conduit system connecting the head assembly and drive frame assembly. Particularly, the head assembly includes a portion fixable to the tube by a pressure bladder and a movable portion helically movable with a probe to the fixable portion. The drive motor and electrical pick-up are slidably movable on the drive frame assembly to move linearly with the probe during inspection so as not to limit the stroke of the probe, wherein the drive motor and pick-up are connected with the head assembly by way of two flexible coaxial conduits. The two conduits further provide two fluid flow paths to supply fluid to the bladder and couplant fluid for use during ultrasonic testing.

36 Claims, 3 Drawing Sheets

SUPPORT EQUIPMENT FOR A COMBINATION EDDY CURRENT AND ULTRASONIC TESTING PROBE FOR INSPECTION OF STEAM GENERATOR TUBING

FIELD OF THE INVENTION

This invention is generally related to a system for helically moving an inspection probe such as a combination eddy current and ultrasonic probe within a heat exchanger tube of a nuclear steam generator by driving the probe from a position outside the steam generator. The inspection probe is driven by way of a system of flexible conduits and a head assembly that fixedly maintains the probe at a set location in a tube while rotational drive is translated into rotational and axial movement at the head assembly to helically move the probe. The system of conduits also defines plural fluid paths to direct fluid such as water into the head assembly for activating a bladder device to secure the head assembly in position as well as to provide fluid to surround an ultrasonic test probe as a medium for ultrasonic testing.

BACKGROUND OF THE INVENTION

The integrity of the heat exchanger tubes in steam generators is of major concern to the nuclear industry for both performance reasons and economic considerations. Periodic inspections of these tubes must be conducted to look for degradation of the tubing, such as denting, pitting, cracking which sometimes occurs in the tubesheet and support plate regions of the generator. As such nuclear steam generators become older, it is becoming increasingly important to develop new techniques of in service inspection for detection of tube degradation.

Eddy current probes and ultrasonic probes for in service inspection of such tubes are known in the prior art. Originally, eddy current in service inspection techniques were developed to detect wall thinning of the heat exchanger tubes. Such eddy current testing was based on the use of alternating current frequency instrumentation in conjunction with electric coil probes. The alternating current conducted through the probe coil created a time varying magnetic field which is turn induced eddy currents in the metallic walls of the heat exchanger tubes. These eddy currents in turn produced counter-magnetic fields that impeded the time varying magnetic field generated by the probe coil. Discontinuities caused by flaws in the metallic walls of the tubes tend to resist the eddy currents, which in turn lowers the impedance that the magnetic fields associated with the eddy currents imposes on the magnetic field of the probe coil. Thus, flaws could be detected by monitoring impedance changes in the coil of the eddy current probe.

As this test procedure evolved, multiple frequency, computer controlled instrumentation systems were used which could be connected to any number of special purpose eddy current probes each, of which was designed to detect a specific type of degradation. However, even with such improvements, eddy current inspection techniques could not detect some types of degradation with any reliability, and in some cases it was difficult or impossible to discriminate between signals produced by combinations of different types of degradation which may occur in a single location in the tube.

As a result, ultrasonic inspection systems have been developed which have been found to more accurately indicate what type of degradation might be present within a particular tube. Like eddy current test procedures, such ultrasonic systems have evolved since their introduction so that they now use sophisticated multi-channel, multi-transducer electronic systems capable of resolving different types of flaws. Such ultrasonic systems take a much longer time to conduct an inspection than eddy current inspection systems, although they do have the advantage of being especially effective in resolving flaws where eddy current testing is the most limited. The complimentary character of the ultrasonic and eddy current inspection techniques has led to the concurrent use of both methods in a combination probe, an example of which is disclosed in U.S. patent application Ser. No. 079,860 filed July 7, 1987, now U.S. Pat. No. 4,856,337, by Warren Junker et al. and assigned to the Westinghouse Electric Corporation.

Ultrasonic testing techniques in a preferred usage require a couplant fluid such as water between the ultrasonic probe and the wall of the tube being tested. The couplant fluid increases the sensitivity of the probe in detecting flaws. In order to run a test, it is necessary to helically move the ultrasonic probe while also supplying the couplant medium around the probe during the testing procedure. In known ultrasonic systems, water couplant was injected into the tube around the ultrasonic probe by way of the same flexible drive shaft that was used to position and helically move the probe within the tube. Keeping the water couplant around the probe was accomplished by a barrel seal located around the flexible drive shaft. In such a known system, the transducer of the probe was moved circumferentially and axially within the tube by means of a screw thread, and the position of the probe relative to the tube wall was determined by means of a rotary encoder connected to the screw thread.

The drive system in this prior art system which rotated the flexible drive shaft was located at and mounted to the tubesheet of the steam generator. From the tubesheet, a flexible shaft was rotatably driven to helically move the ultrasonic probe within the steam generator tubing. However, this type system was limited in that the probe could only be extended into the tubes to a height of only about two meters above the tubesheet. Since the legs of the heat exchanger tubes are about 10 meters long, much of the tubing could not be inspected. Additionally, this system was cumbersome to move from tube to tube within the tubesheet.

To overcome these limitations, a drive system was developed that incorporated a miniature drive motor coupled to a rotary encoder device that could be inserted into the tube along with the probe body. This arrangement circumvented the previous limitation on probe height above the tubesheet, and the probe could be positioned anywhere up to the start of the U-bend of the tube. This drive system was also an improvement over the tubesheet mounted drive system in that the probe and its drive system could be easily moved from tube to tube with the use of known robots.

This drive system consists of a miniature motor coupled in tandem with a gear box and a screw mechanism that was mounted at the probe end which the probe itself was attached. This system also included an expandable, fluid actuated bladder which circumscribed the probe body for maintaining the position of the probe within the tube, and a slip ring arrangement that allowed electrical power to be conducted to the motor and to the probe. Unfortunately, this drive system has not proven to be entirely satisfactory due in part to the power limitation associated with the small size of the motor. It also has proven difficult to completely seal the electrical components such as the motor and slip ring arrangement from the couplant water. Finally, it has proven to be very difficult to effectively prevent the electrical wires between the probe and the slip ring arrangement from binding or tangling during the operation of the device, as a result of the distance changes between the probe and the slip ring as the screw mechanism axially moves the probe relative to the slip ring arrangement. In an attempt to solve this last problem, the wires were loosely coiled in an orifice within the cartridge to provide the required slack. However, the scan length was still limited to only about 2.5 cm with each location of the probe by the bladder. Thus, it was necessary to relocate the entire probe assembly many times to inspect even a decimeter of tubing. Since ultrasonic testing is in itself a slow process, the process was unreasonably lengthened by having to relocate the probe assembly so many times to do an inspection of any significant length of tubing.

Clearly, there is a need for a drive system that can helically move an inspection probe assembly having an ultrasonic probe over a greater stroke distance than prior art systems, and which has a sufficient torque to rotatably drive the probe while maintaining the electrical components safe from couplant water. Ideally, the drive system should allow the probe assembly to be easily moved from tube to tube, and should be highly reliable in operation.

SUMMARY OF THE INVENTION

In its broadest sense, the invention is an improved apparatus for helically moving an inspection probe within a tube steam generator, wherein the probe can be moved over an increased stroke length while providing sufficient torque and avoiding electrical shorting. The system generally comprises a head assembly connectable to the inspection probe including a movable portion and a portion fixable to the tube to be inspected, and a drive frame assembly having a drive motor operably connected to a first conduit that is further connected to the movable portion of the head assembly. A second conduit is also included that is coaxial to the first conduit to together define two fluid paths wherein water can be supplied for providing a couplant that surrounds the probe in use as well as a hydraulic fluid for expanding a bladder located on the fixable portion of the head assembly that detachably mounts the head assembly within a selected tube.

The apparatus includes a rigid shaft element fixed to an end of the first flexible conduit that is provided internally within the head assembly, wherein the rigid shaft is further fixed to the movable portion of the head assembly and includes a threaded portion adjacent to the end fixed to the movable portion that engages with a co-operating threaded element of the fixable portion. Thus, when the first flexible shaft is rotated by the drive motor, the rigid shaft is rotated, and by means of the co-operating threaded engagement between the rigid shaft and the fixable portion of the head assembly, the movable portion of the head assembly is rotatably and axially moved to define a helical pattern of movement for a probe connected to the movable portion. Moreover, on the fixable portion of the head assembly, the bladder is provided radially outward of the rigid shaft that passes through the fixable portion, and water conducted between the first and second conduits can pass into the bladder device so as to expand the bladder to detachably secure the fixable portion to a tube of a steam generator. The bladder has the further advantageous function of sealing the head assembly to the tube so that when couplant water is provided through the first conduit to the probe, the bladder secondarily prevents that couplant water from draining back through the tube. Additionally, between the rotatable rigid shaft and the fixable portion of the head assembly, an encoder device is included to monitor the position of an inspection probe by counting the number of rotations of the rigid shaft.

The first and second conduits are connected to the drive frame assembly through a series of pipes, couplings and T-connectors, so that water can be independently supplied internal of the first conduit for couplant and between the first and second conduit for the bladder without interference with each other and without leakage of the water into the drive motor area and electrical portion of the drive frame assembly.

The drive frame assembly includes a rigid frame onto which the drive motor is slidably connected so that as the probe and first conduit are moved axially by the threaded engagement within the head assembly, the drive motor will move accordingly. The drive frame assembly further includes a limit switch device which moves at a same stroke distance as the probe within a tube by using like threaded elements. The limit switch device defines end limits to the stroke length of travel of the probe to prevent damage to the probe at either end of travel. This limit switch device secondarily provides a positive axial pulling or pushing of the drive motor and conduit from the end opposite the head assembly. If the head assembly pulls the conduits, the limit switch device provides a positive push from the drive assembly side, and vice versa.

Additionally, the electrical wires, consisting of preferably five coaxial cables, extend from the probe through the head assembly and first conduit into the drive frame assembly, whereat the coaxial cables are appropriately wired with a slip ring arrangement that is also axially movable with the first conduit. Thus, it is not necessary to compensate for axial movement of the wires within the head assembly, conduit or drive device because the slip ring arrangement moves with the conduits and wires.

The drive motor, limit switches, and cables coming from the slip ring arrangement are appropriately wired to a control and monitoring system that controls the operation of the probe and reads the information transmitted from the probes. This would include the sensing of both eddy current and ultrasonic testing probes. The signals from the probes can then be processed and evaluated by the system operator.

BRIEF DESCRIPTION OF THE SEVERAL FIGURES

DETAILED DESCRIPTION OF THE PREFERRED EMBODIMENT

Figure 1:
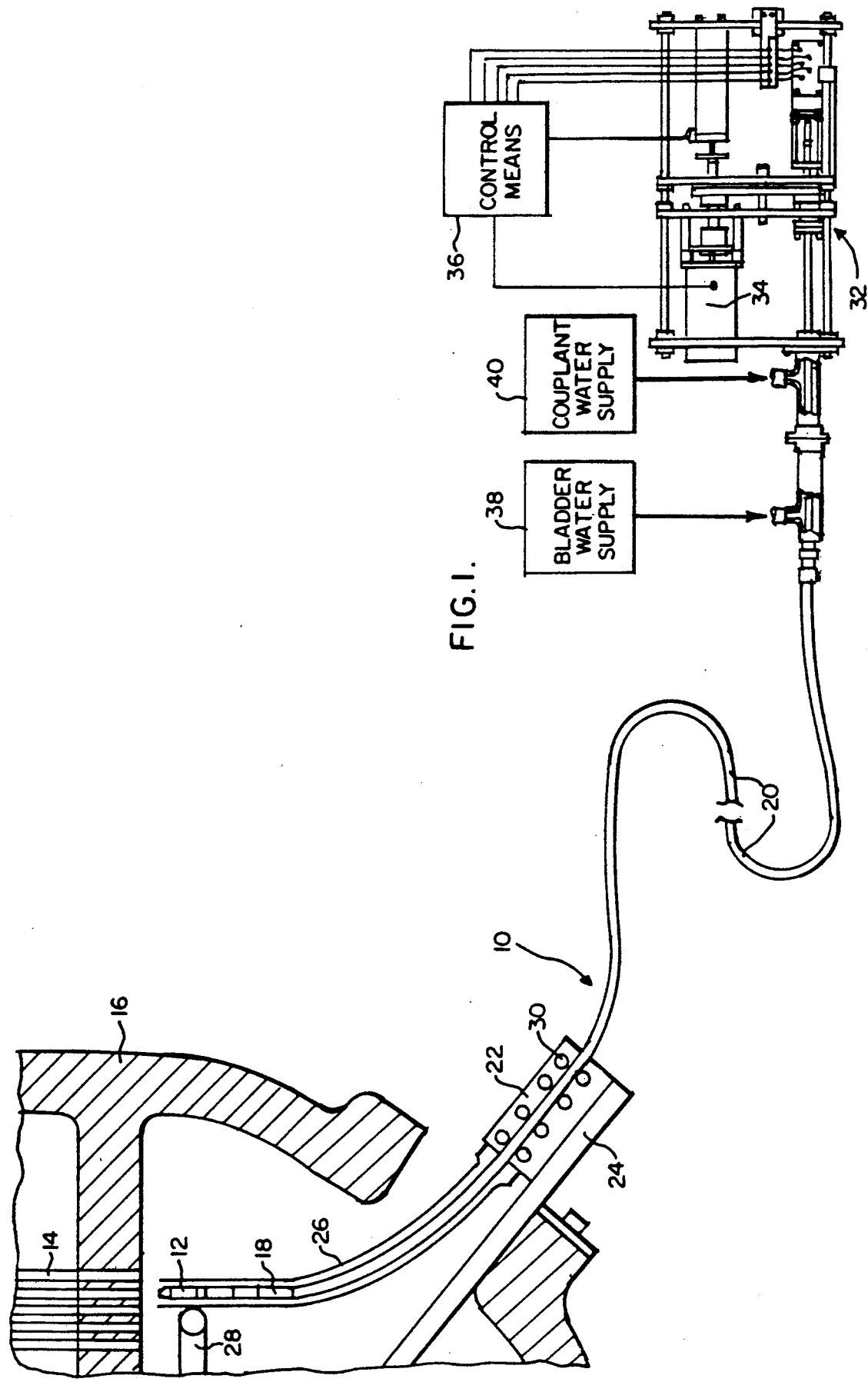
FIG. 1 is a schematic illustration showing the apparatus and system of the present invention including a portion of a steam generator and an inspection probe to be driven into a steam generator heat exchanger tube.

With reference now to the several figures and in particular to FIG. 1, wherein like numerals designate like components throughout all of the several figures, a support system 10 for an inspection probe, particularly a combination eddy current and ultrasonic inspection probe, is illustrated. The support system 10 is shown for the positioning and driving of an inspection probe 12 within any one of the tubes 14 of a steam generator 16. In FIG. 1, only a few of the heat exchanger tubes 14 are illustrated; however, many hundreds or thousands of such tubes may be present in a single steam generator depending on the size thereof.

The inspection probe 12 is detachably connectable to a head assembly 18 by electrical pins which is in turn connected to a conduit system 20, that flexibly permits the insertion and positioning of the inspection probe 12 in a tube 14. In order to position the inspection probe 12 within a tube 14, a probe pusher 22 is secured to the steam generator 16 by a mounting platform 24, and the probe 12 is guided toward a particular tube by a guide sleeve 26 connected at one of the probe pusher 22. The other end of the guide sleeve 26 is movably positionable under any one of the tubes 14 by way of a known remotely controlled device, of which an arm 28 is shown attached to the guide sleeve 26. The manner in which the arm 28 is controlled does not form a particular part of the present invention, and can be associated with any robotic device or system as are presently used for positioning guide devices in steam generators. The probe pusher 22 includes drive rollers 30 which are appropriately driven by a single motor or series of motors in accordance with known principles. Thus, conduit system 20 can be driven to insert or remove the head assembly 18 and inspection probe 12 within any one of the tubes 14.

The support system 10 further includes a drive frame assembly shown generally at 32 which includes a drive motor 34 that provides a rotational drive that is transferred to the inspection probe 12 by way of the head assembly 18 and the conduit system 20. The manner in which the rotational drive is transferred will be understood with the detailed description of the head assembly 18, conduit system 20 and drive frame assembly 32 below.

Furthermore, the support system 10 includes a monitoring and control means 36 that controls all of the driving features of the drive frame assembly 32, as well as the picking up of the signals sensed from the inspection probe 12, these signals being carried by way of flexible coaxial cables from the probe 12 to the drive frame assembly 32. Also provided as elements of the system 10 are a bladder water supply 38 and a couplant water supply 40, the reasons for which will be apparent with the description below.

Figure 2:
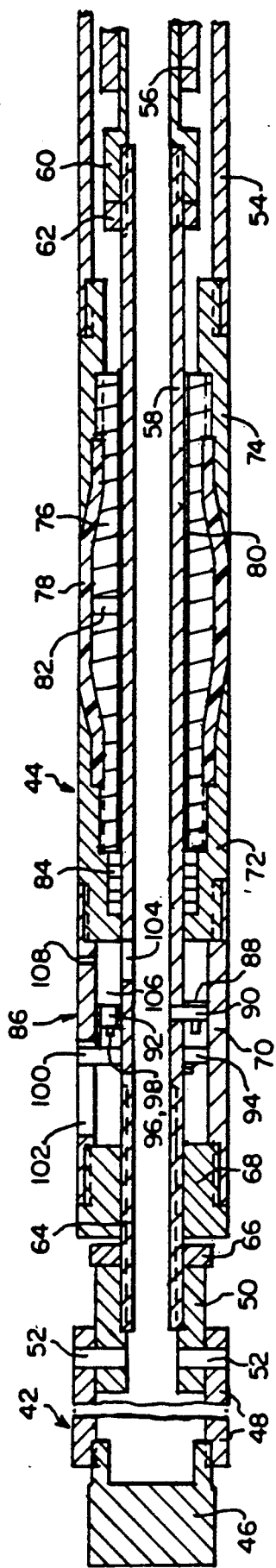
FIG. 2 is a cross-sectional view of the head assembly of the present invention.

With reference now to FIG. 2, the head assembly 18 will be described. The head assembly 18 is basically comprised of two portions which are relatively movable with respect to one another, including a movable portion 42 and a fixable portion 44. The movable portion 42 includes a probe attachment and electrical connector element 46 having quick connect electrical connections of the pin type, which are to engage with cooperating pin type connectors of a probe unit attached thereto. Preferably, with a combination ultrasonic and eddy current probe, there should be at least eight pins of which six are for the ultrasonic sensors and two are for the eddy current sensors. It is preferable to include 12 pin connections to accommodate additional probe wires as necessary. The movable portion 42 further includes a sleeve 48 which is threadingly attached to the attachment and connector element 46, for example by standard pipe threads, and is further connected at the opposite end to an inner sleeve 50 by pins 52. Thus, elements 46, 48 and 50 are movable together in both rotational and axial directions.

As can be seen at the right hand side of FIG. 2, the conduit system 20 includes an outer conduit 54 and a coaxial inner conduit 56. Both conduits 54 and 56 are flexible in nature, and the inner conduit 56 is preferably made of a material sufficient to transmit torque from said drive frame assembly 32. Preferably a stainless steel convoluted tubing is used for the inner conduit. The inner conduit 56 is connected to a rigid shaft 58 by way of a sleeve 60 and lock ring 62. The sleeve 60 is preferably welded or brazed to the inner conduit 56 and threadedly connected to the rigid shaft 58 with the aid of lock ring 62. Rigid shaft 58 is a hollow shaft that extends from a point adjacent the inner conduit 56 all the way through the fixable portion 44 of the head assembly 18 and into the movable portion 42, at inner sleeve 50. This rigid shaft 58 is provided with a threaded portion 64 adjacent the end fixed to the movable portion 42, and the inner sleeve 50 is threadingly connected to the rigid shaft 58 and is secured in place held on by lock ring 66. Thus, it can be seen that the rigid shaft 58 and flexible inner conduit 56 move with the movable portion 42 of the head assembly 18.

The fixable portion 44 of the head assembly 18 is comprised of an end fitting 68, a first sleeve 70, a second sleeve 72, a third sleeve 74, and a bladder support 76. The bladder support 76 is connected between the second and third sleeves 72 and 74 respectively, and the first sleeve 70 is connected between end fitting 68 and the second sleeve 72. Thus, a rigid structure is maintained from end fitting 68 through the third sleeve 74, which is then further attached to the flexible outer conduit 54. It is also contemplated that additional rigid sleeves may be provided between the end of the outer conduit 54 and the third sleeve 74, as may be required to provide a longer rigid head assembly.

The end fitting 68 is provided with internal threads that co-operate with the external threads of the threaded area 64 on the rigid shaft 58. Therefore, as rigid shaft 58 is rotated by the inner conduit 56, the rotational movement will be translated into both rotational and axial movement by end fitting 68 when the fixable portion 44 is fixedly maintained with regard to rotational movement. Thus, helical movement of the movable portion 42 and a probe attached thereto is produced by the rotation of the inner conduit 56. Such helical movement being necessary for ultrasonic testing of a steam generator tube. As the inner conduit 56 is rotated, the movable portion 42, rigid shaft 58, and inner conduit 56 will move together either to the right or to the left as viewed in FIG. 2.

Also provided on the fixable portion 44 is a bladder 78 which is used to rotationally and axially maintain the head assembly 18 at a specific location within a steam generator tube. This bladder 78 is made up of a expandable elastomeric material which is supplied with a pressurized fluid causing the bladder 78 to expand and lock against the side walls of a tube. The fluid could be gaseous or liquid pressurized.

In order for a pressurized fluid, preferably water, to expand the bladder 78, the fluid is provided between the inner and outer conduits 56 and 54 respectively under pressure, and the pressurized fluid travels between the rigid shaft 58 and the bladder support 76 through the clearance area 80 and subsequently through an opening 82 in bladder support 76. The clearance 80 shown between the rigid shaft 58 and the bladder support 76 is actually no more than five to ten thousands of an inch, however, the clearance 80 is exaggerated in FIG. 2 for the sake of illustration. Additionally, to insure that the pressurized fluid does not go any further than the bladder area, a series of seals 84 are provided surrounding the rigid shaft 58. Thus defined is a first fluid path passing between the conduits 54 and 56 to supply pressurized fluid to the bladder 78 for expansion thereof so as to lock the head assembly 18 to a steam generator tube. After the fixable portion 44 of the head assembly 18 is maintained with respect to a heat exchanger tube, the movable portion 42 can be moved axially and rotationally by driving inner conduit 56.

An encoder 86 is also provided within the head assembly 18 for accurately keeping track of the axial position of a probe secured to the movable portion 42. To accomplish this, a disk shaped element 88 is fixed to the rigid shaft 58 by a set screw 90. The disk member 88 further includes an eddy current probe at 92. Rotatably mounted on the rigid shaft 58 is a second disk shape member 94 that is provided with a plurality of ferrite slugs 96 and one copper slug 98. In order to keep the second disk member 94 from rotating with the rigid shaft 58, an extension element 100 extends radially outward through a slot 102 provided in the first sleeve 70 of fixable portion 44. As a result, the eddy current probe 92 senses the passing of each of the ferrite slugs 96 and the copper slug 98, which happens because the first disk shaped member 88 rotates with the rigid shaft 58 while the second disk member 94 is rotationally non-movable. The slot 102, also permits the second disk 94 to slide with respect to the fixable portion 44 as the movable portion 42 moves axially. Each full rotation is measured by each passing of the copper slug 98, while portions of a rotation are measured by counting each ferrite slug 96. Because the pitch of the threads between end fitting 68 and rigid shaft 58 is known, the amount of axial displacement can be accurately detected by the encoder 86 by monitoring the rotation.

Electrical cables, preferably coaxial cables, (not shown) extend from the connector 46 through sleeve 50 to carry signals from the inspection probe, and another cable extends from the eddy current probe 92 of the encoder 86 through opening 104. These cables extend through the rigid shaft 58 and subsequently through the inner conduit 56 all the way down to the drive frame assembly 32, as described below.

Additionally, the inner conduit 56 and hollow rigid shaft 58 are used to provide a couplant fluid therethrough, which is used in an ultrasonic testing inspection process. In such a process, a couplant fluid such as water, must be provided surrounding the ultrasonic transducer within the tube to be inspected. Thus, in order to fill the area around the ultrasonic probe, couplant fluid flows under pressure into the rigid shaft 58 and exits through an opening 104 into a chamber 106 within sleeve 70, and subsequently out of chamber 106 through opening 108. Couplant fluid is supplied until the probe senses sufficient couplant fluid for inspection to take place. The bladder 78, secondarily, seals the head assembly 18 to the steam generator tube so that the couplant fluid will not flow down around the tubing, but will be maintained above the bladder 78 to the point necessary for the ultrasonic probe to operate. Upon completion of the ultrasonic scan, the couplant fluid can be recovered by being drawn back through opening 108; and only the amount between opening 108 and bladder 78 is lost. This almost complete recovery of couplant advantageously provides for better control of the contaminated water.

Figure 3:
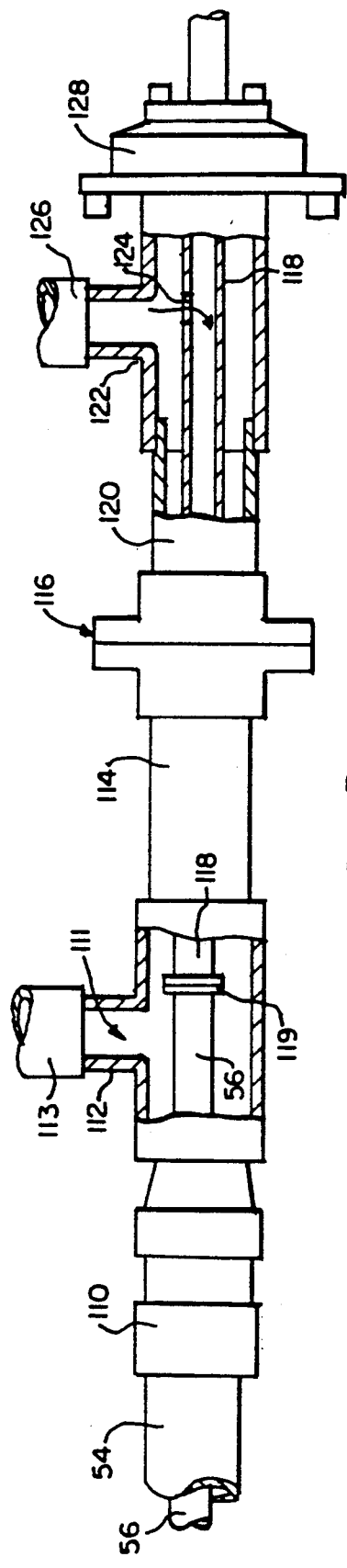
FIG. 3 is a side view, partially in crosssection, of the conduit assembly of the present invention showing the manner of water supply.

With reference now to FIG. 3, the manner in which bladder fluid and fluid couplant are provided to the head assembly 18 will be described. The inner and outer conduits 56 and 54 respectively are seen at the left hand side of FIG. 3. Outer conduit 54 terminates in a swage lock fitting 110 (compression-type fitting), which is further connected to a first T-fitting 112. The first T-fitting 112 has an opening at 111 which is connected to a water supply pipe 113 providing pressurized water. The water fills the space between the inner conduit 56 and the external walls of the T-fitting 112 and subsequently the space between the inner conduit 56 and the outer conduit 54. The T-fitting 112 is further connected by way of a sleeve 114 to a seal assembly 116, which prevents the back flow of water between conduits 54 and 56 from the T-fitting 112 beyond the seal 116. That is, the pressurized water supplied by the first water supply does not flow to the right of seal 116 as viewed in FIG. 3. Preferably, seal assembly 116 includes conventional ball seals.

At some point within the above-described pipe assembly, the inner conduit 56 is attached to a rigid conduit 118 by a flange assembly 119 (shown within T-fitting 112), and rigid conduit 118 extends through the seal assembly 116 and through a second sleeve 120 as well as a second T-fitting 122. Within the second T-fitting 122, the rigid conduit 118 includes an opening 124 through which pressurized water can pass that is supplied from a second water supply pipe 126. The seal assembly 116 with a second seal assembly 128 together confine the pressurized water outside of the rigid conduit 118 so that the only way for the pressurized water to travel is through the opening 124 into rigid conduit 118 and subsequently to the inner conduit 56. It is noted that the electrical cables coming from the inspection probe and head assembly 18 also pass within the inner conduit 56 and rigid conduit 118. Therefore, it is also necessary to provide a seal within the rigid conduit 118 that permits the wires to pass through at the area where the rigid conduit 118 passes through the seal assembly 128. In order to accomplish this, a sealant such as RTV or silicone sealant can be used preventing water passage but permitting the wires to extend therethrough. Thus, rigid conduit 118 extends out of the seal assembly 128 with only the electrical wires therein.

Figure 4:
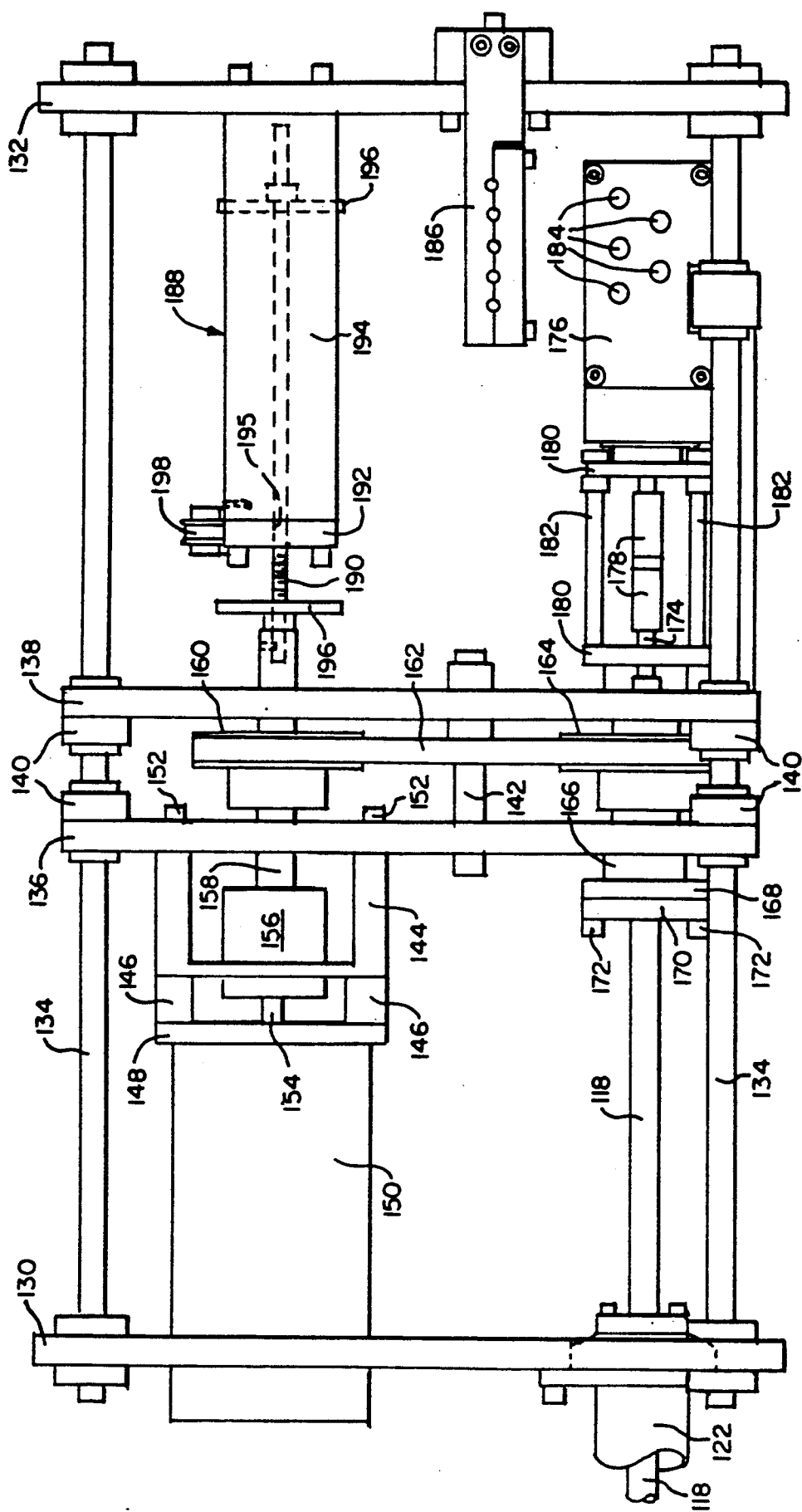
FIG. 4 is a side view of the drive frame assembly of the present invention.

Referring now to FIG. 4, it can be seen at the lower left hand portion that rigid conduit 118 extends into the drive frame assembly 32. The drive frame assembly 32 is basically comprised of a first end plate 130 and a second end plate 132. Extending between the end plates 130 and 132 are a plurality, preferably 4, of support rods 134. Slidably attached to the support rods 134 are two plates 136 and 138 by way of slide bushings 140. The slide plates 136 and 138 are fixedly spaced with respect to one another by a spacer assembly 142. Mounted to the slide plate 136 by way of a support bracket 144, electrical insulators 146 and plate 148 is a drive motor 150. The support bracket 144 is connected to the slide plate 136 by way of conventional bolts or cap screws 152. The output shaft of the motor 154 is connected by way of an electrically non-conductive coupler unit 156 to a driven shaft 158. A sprocket 160 is rotationally fixed to the driven shaft 158, so as to drive a timing belt or chain 162 which in turn drives a second sprocket 164 rotationally secured to a second driven shaft 166. Element 168 is rotationally fixed with second driven shaft 166, and is further connected to a clamp assembly 170 by bolts 172. The clamp assembly 170 is rotationally clamped to the rigid conduit 118, so that rotational drive torque is transferred from second driven shaft 166 to the rigid conduit 118. As a result, the inner conduit 56, rigid shaft 58, and movable portion can be rotationally driven.

Since, as above described, the rotational drive within the head assembly causes an axial shifting of the rigid shaft 58 and inner conduit 56, it follows that rigid conduit 118 and thus the entire described drive means must also move axially. In this regard, the sliding plates 136 and 138 facilitate this axial movement by sliding on support rods 134.

The second driven shaft 166 is a hollow shaft that permits the rigid conduit 118 to pass therethrough thus guiding the electrical wires through the drive system. The electrical wires indicated at 174 exit the rigid conduit 118, and pass into a slip ring assembly housing 176 by way of connectors 178. Since the cables 174 move rotationally with the inspection probe 12 at the other end of the system, it is necessary to accommodate the rotation of the wires at the drive assembly end as well. In order to do this, a device consisting of end plates 180 and rods 182 are also rotationally driven by the second driven shaft 166. Thus, as the cables 174 enter the slip ring housing 176, they are rotating at the same speed as the inspection probe. It is then necessary to utilize a multiple unit slip ring assembly within the housing 176 that picks up the electrical signals of the rotating wires as is conventionally known. Stationary wires then exit the slip ring housing 176 at connectors 184 from which appropriate wiring will be run to the monitoring and control means 36, as seen in FIG. 1.

The slip ring housing 176 and the wire turning assembly 180 and 182 are also slidably mounted on two of the support rods 134 so that the slip ring housing 176 moves along with the axial movement of the drive means, the rigid conduit 118, the inner conduit 56, the rigid shaft 58, and the movable portion 42. As a result, it is unnecessary to compensate for axial movement of the probe in the wiring system, and the wiring will not limit the stroke travel of the probe. A wiring harness 186 is fixed with the plate 132 of the non-moving portion of the frame assembly 32; however, plenty of slack can be easily provided between the wiring harness 186 and the connectors 184 without any problem relating to the stroke distance.

Additionally, the drive frame assembly 32 includes a supplemental driving device and limit switch means at 188. This supplemental drive and limit switch means 188 consists of a threaded shaft 190 rotationally and axially fixed with the driven shaft 158. The threaded shaft 190 passes through a plate 192 fixed with respect to the non-movable support plate 132 by a U-shaped bracket 194. The plate 192 includes a through bore 195 with complementary threads to the threaded shaft 190. The pitch of the threads on shaft 190 and bore 195 are the same as the pitch of the threads of elements 58 and 68 within the head assembly 18. Thus, as the threads in the head assembly attempt to pull or push the conduits and drive assembly, the supplemental action of the threaded shaft 190 and plate 192 will push or pull respectively. Furthermore, threaded shaft 190 includes trigger plates 196 that define the stroke distance of the entire axial length of the probe therebetween. As the threaded shaft 190 moves axially as a result of the rotational drive of the driven shaft 158, one of the trigger plates 196 will be moved towards a set of limit switches 198, upon contact with one of the set of switches of 198, the motor will be shut off. The limit switch is appropriately wired to the control means 36.

In operation, once the inspection probe 12 has been provided within a steam generator tube 14 for inspection, pressurized water is supplied from the bladder supply tank 38 between the inner conduit 56 and the outer conduit 54 and to the bladder 78. Thus, the fixable portion 44 of the head assembly 18 is secured to the steam generator tube. Thereafter, the couplant supply 40 is activated sending pressurized fluid through the inner conduit 56 until it exits opening 104 within the rigid shaft 58. The couplet fluid then fills the void space formed above the bladder 78 with couplant until a sensor on the inspection probe indicates that the couplant has been sufficiently provided. Next, the drive motor 150 is operated so as to rotationally drive rigid conduit 118 and thus the inner conduit 56, rigid shaft 58 and movable portion 42 of the head assembly 18. The cooperating threads between elements 68 of the fixable portion 44 and the threads at 64 on the rigid shaft 58 translate the rotational drive into rotational as well as axial movement of the movable portion 42 and thus the inspection probe secured thereto. The helical travel path of the inspection probe is thereby defined. In the meanwhile, the slip ring housing 176 and supplemental drive and limit switch means 188 axially move along with the entire drive system in a like manner as the inspection probe within the tube. All the while, the monitoring and control means 36 is monitoring the signals received from the probe and controls the operation of the drive motor 150. Lastly, when one of the trigger plates 196 contacts one of the limit switches 198, the operation is stopped because the full stroke of probe travel has been completed. Thereafter, further inspection requires a repositioning of the head assembly 18.

I claim:

1. An apparatus for helically moving an inspection probe within a tube comprising:
   a. a head assembly for insertion within a tube to be inspected and for helically moving an inspection probe therein along a longitudinal axis of the tube, said head assembly comprising a first portion having means to fix said first portion to an internal surface of a tube at a location along the tube, and a second portion movably connected to said first portion by conversion means that converts driven rotary motion of said second portion about the longitudinal axis of the tube into rotary and axial motion of said second portion, said second portion including means for detachably connecting an inspection probe to said second portion for moving the inspection probe with said second portion of said head assembly; and b. a drive frame assembly for imparting the driven rotary motion to said second portion from a location external of the tube by way of a conduit means, said drive frame assembly having a drive motor slidably mounted thereon that is operably connected to said conduit means for driving the rotary motion imparted to said second portion by way of said conduit means connected between said drive motor and said second portion, wherein said drive motor is slidably moved in a linear direction by said conduit means when said axial motion of said second portion is provided by said conversion means.

2. The apparatus of claim 1, wherein said conduit means includes a first conduit connected between said second portion of said head assembly and said drive motor for transferring driven rotary motion from said drive motor to said second portion and a second conduit coaxial to and external to said first conduit connected between said first portion of said head assembly and said drive frame assembly.

3. The apparatus of claim 2, wherein said first conduit is connected to said second portion by way of a rigid shaft that passes through a hollow interior of said first portion, said rigid shaft having external threads located along a portion of said rigid shaft and said first portion having internal threads within said hollow interior that cooperate with said external threads of said rigid shaft to provide said conversion means, whereby rotary motion from said drive motor causes helical motion of said second portion relative to said first portion.

4. The apparatus of claim 3, wherein said means to fix said first portion to an internal surface of a tube comprises an expandable bladder.

5. The apparatus of claim 4, wherein said expandable bladder opens to a first fluid flow path comprising a space formed between an external surface of said first conduit and an internal surface of said second conduit, and a fluid supply means for communicating pressurized fluid to said space.

6. The apparatus of claim 5, including a second fluid flow path for providing couplant fluid to said head assembly, said second fluid flow path comprising a hollow interior extending through said first conduit and said rigid shaft, an opening in said rigid shaft within said first portion of said head assembly, an opening through said first portion, and a couplant supply means for communicating pressurized fluid to said interior hollow.

7. The apparatus of claim 6, wherein said fluid supply means includes a first T-fitting connected to said second conduit, and said couplant supply means includes a second T-fitting connected to said second conduit at a point further away from said head assembly than said first T-fitting and an opening in said first conduit substantially at said second T-fitting, said second T-fitting being bounded by seal means at upstream and downstream sides thereof to prevent communication between said first fluid flow path and said second fluid flow path.

8. The apparatus of claim 1, wherein said drive frame assembly comprises two plates with at least one guide rail extending therebetween, and said drive motor includes a complimentary guide device slidable on said guide rail.

9. The apparatus of claim 8, wherein said conduit means includes a rigid conduit portion that extends within said drive frame assembly, said conduit means also guiding electrical cables from said means for detachably connecting an inspection probe to said head assembly to a slip ring assembly also slidably mounted to said frame assembly to move linearly with said second portion of said head assembly.

10. The apparatus of claim 9, wherein said drive motor operatively drives said rigid conduit portion of said conduit means by way of a transfer means so that the axis of a motor shaft of said drive motor is parallel to the axis of said rigid conduit portion.

11. The apparatus of claim 10, wherein said slip ring assembly is slidably mounted on another guide rail extending between said plates to move along an axis parallel to the axis of said rigid conduit portion, and said electrical cables extend from an opening at the axial end of said rigid conduit portion.

12. The apparatus of claim 11, further including a supplemental means within said drive frame assembly to impart linear motion to said drive motor, said slip ring assembly and said conduit means, said supplemental means comprising a fixed element secured to said drive frame assembly having a threaded bore coaxial with said motor shaft and a externally threaded shaft rotationally and axially fixed to said motor shaft, said threaded shaft cooperating with said threaded bore to move said drive motor at a like degree and like direction as the conversion means moves said second portion of said head assembly.

13. The apparatus of claim 12, wherein said supplemental means further includes limiting means comprising two trigger plates axially mounted to said threaded shaft to move therewith with a maximum stroke distance of the drive motor and second portion of said head assembly defined between said trigger plates, and a limit switch mounted to said fixed element of said supplemental means which when abutted by either of said trigger plates ceases operation of said drive motor.

14. An apparatus for helically moving an inspection probe within a tube comprising:

a. a head assembly for insertion within a tube to be inspected and for helically moving an inspection probe therein along a longitudinal axis of the tube, said head assembly comprising a first portion having means to fix said first portion to an internal surface of a tube at a location along the tube, and a second portion movably connected to said first portion by conversion means that converts driven rotary motion of said second portion about the longitudinal axis of the tube into rotary and axial motion of said second portion, said second portion including means for detachably connecting an inspection probe to said second portion for moving the inspection probe with said second portion of said head assembly; and b. a drive frame assembly for imparting the driven rotary motion to said second portion from a location external of the tube by way of a conduit means, said conduit means comprising two coaxial conduits with a first conduit internal of a second conduit, said first conduit is connected to said second portion by a rigid shaft that passes through a hollow interior of said first portion, said drive frame assembly having a drive motor slidably mounted thereon that is operably connected to said first conduit for driving the rotary motion imparted to said second portion by way of said first conduit, wherein said drive motor is slidably moved in a linear direction by said first conduit when said axial motion of said second portion is provided by said conversion means.

15. The apparatus of a claim 14, wherein said second conduit is connected between said first portion of said head assembly and said drive frame assembly.

16. The apparatus of claim 15, wherein said first and second conduits are comprised of flexible shafts.

17. The apparatus of claim 14, wherein said rigid shaft has external threads located along a portion of said rigid shaft, and said first portion has internal threads within said hollow interior that cooperate with said external threads of said rigid shaft thus providing said conversion means, whereby rotary motion from said drive motor causes helical motion of said second portion relative to said first portion.

18. The apparatus of claim 17, wherein said means to fix said first portion to an internal surface of a tube comprises an expandable bladder.

19. The apparatus of claim 18, wherein said expandable bladder opens to a first fluid flow path comprising a space formed between an external surface of said first conduit and an internal surface of said second conduit, and a fluid supply means for communicating pressurized fluid to said space.

20. The apparatus of claim 19, including a second fluid flow path for providing couplant fluid to said head assembly, said second fluid flow path comprising a hollow interior extending through said first conduit and said rigid shaft, an opening in said rigid shaft within said first portion of said head assembly, an opening through said first portion, and a couplant supply means for communicating pressurized fluid to said interior hollow.

21. The apparatus of claim 20, wherein said fluid supply means includes a first T-fitting connected to said second conduit, and said couplant supply means includes a second T-fitting connected to said second conduit at a point further away from said head assembly than said first T-fitting and an opening in said first conduit substantially at said second T-fitting, said second T-fitting being bounded by seal means at upstream and downstream sides thereof to prevent communication between said first fluid flow path and said second fluid flow path.

22. The apparatus of claim 21, wherein said drive frame assembly comprises two plates with at least one guide rail extending therebetween, and said drive motor includes a complimentary guide device slidable on said guide rail.

23. The apparatus of claim 22, wherein said first conduit includes a rigid conduit portion that extends within said drive frame assembly, said first conduit also guiding electrical cables from said means for detachably connecting an inspection probe of said head assembly to a slip ring assembly also slidably mounted to said frame assembly to move linearly with said second portion of said head assembly.

24. The apparatus of claim 23, wherein said drive motor operatively drives said rigid conduit portion of said first conduit by way of a transfer means so that the axis of a motor shaft of said drive motor is parallel to the axis of said rigid conduit portion.

25. The apparatus of claim 24, wherein said slip ring assembly is slidably mounted on another guide rail extending between said plates to move along an axis parallel to the axis of said rigid conduit portion, and said electrical cables extend from an opening at the axial end of said rigid conduit portion.

26. The apparatus of claim 25, further including a supplemental means within said drive frame assembly to impart linear motion to said drive motor, said slip ring assembly and said first conduit, said supplemental means comprising a fixed element secured to said drive frame assembly having a threaded bore coaxial with said motor shaft and a externally threaded shaft rotationally and axially fixed to said motor shaft, said threaded shaft cooperating with said threaded bore to move said drive motor at a like degree and like direction as the conversion means moves said second portion of said head assembly.

27. The apparatus of claim 26, wherein said supplemental means further includes limiting means comprising two trigger plates axially mounted to said threaded shaft to move therewith with a maximum stroke distance of the drive motor and second portion of said head assembly defined between said trigger plates, and a limit switch mounted to said fixed element of said supplemental means which when abutted by either of said trigger plates ceases operation of said drive motor.

28. An apparatus for helically moving a combination eddy current and ultrasonic test inspection probe within a tube of a nuclear generator comprising:

a. a head assembly for insertion within a tube to be inspected and for helically moving an inspection probe therein along a longitudinal axis of the tube, said head assembly comprising a first portion having means to fix said first portion to an internal surface of a tube at a location along the tube, and a second portion movably connected to said first portion by conversion means that converts driven rotary motion of said second portion about the longitudinal axis of the tube into rotary and axial motion of said second portion, said second portion including means for detachably connecting an inspection probe to said second portion for moving the inspection probe with said second portion of said head assembly; and b. a drive frame assembly for imparting the driven rotary motion to said second portion from a location external of the tube by way of a conduit means, said drive frame assembly having a drive motor slidably mounted thereon that is operably connected to said conduit means for driving the rotary motion imparted to said second portion by way of said conduit means connected between said drive motor and said second portion, wherein said drive motor is slidably moved in a linear direction by said conduit means when said axial motion of said second portion is provided by said conversion means, wherein said conduit means includes a first conduit connected to said second portion by a rigid shaft passing through a hollow interior of said first portion, said rigid shaft having a threaded portion cooperating with internal threads on said first portion in said hollow interior to provide said conversion means, said first conduit further connected to said drive motor, and a second conduit connected between said first portion and said drive frame assembly, said conduit means further defining a first fluid flow path comprising a space formed between an external surface of said first conduit and an internal surface of said second conduit, and a second fluid flow path comprising a hollow interior of said first conduit and said rigid shaft, said first fluid flow path connected to a fluid supply means for providing pressurized fluid to said means to fix said first portion, and said second fluid flow path connected to a couplant fluid supply means for providing pressurized fluid to said head assembly for surrounding an inspection probe within a tube with couplant fluid for ultrasonic testing to the tube.

29. The apparatus of claim 28, wherein said fluid supply means includes a first T-fitting connected to said second conduit, and said couplant supply means includes a second T-fitting connected to said second conduit at a point further away from said head assembly than said first T-fitting and an opening in said first conduit substantially at said second T-fitting, said second T-fitting being bounded by seal means at upstream and downstream sides thereof to prevent communication between said first fluid flow path and said second fluid flow path.

30. The apparatus of claim 29, wherein said drive frame assembly comprises two plates with at least one guide rail extending therebetween, and said drive motor includes a complimentary guide device slidable on said guide rail.

31. The apparatus of claim 30, wherein said first conduit includes a rigid conduit portion that extends within said drive frame assembly, said conduit also guiding electrical cables from said means for detachably connecting an inspection probe of said head assembly to a slip ring assembly also slidably mounted to said frame assembly to move linearly with said second portion of said head assembly.

32. The apparatus of claim 31, wherein said drive motor operatively drives said rigid conduit portion of said first conduit by way of a transfer means so that the axis of a motor shaft of said drive motor is parallel to the axis of said rigid conduit portion.

33. The apparatus of claim 32, wherein said slip ring assembly is slidably mounted on another guide rail extending between said plates to move along an axis parallel to the axis of said rigid first conduit portion, and said electrical cables extend from an opening at the axial end of said rigid conduit portion.

34. The apparatus of claim 33, further including a supplemental means within said drive frame assembly to impart linear motion to said drive motor, said slip ring assembly and said first conduit, said supplemental means comprising a fixed element secured to said drive frame assembly having a threaded bore coaxial with said motor shaft and a externally threaded shaft rotationally and axially fixed to said motor shaft, said threaded shaft cooperating with said threaded bore to move said drive motor at a like degree and like direction as the conversion means moves said second portion of said head assembly.

35. The apparatus of claim 34, wherein said supplemental means further includes limiting means comprising two trigger plates axially mounted to said threaded shaft to move therewith with a maximum stroke distance of the drive motor and second portion of said head assembly defined between said trigger plates, and a limit switch mounted to said fixed element of said supplemental means which when abutted by either of said trigger plates ceases operation of said drive motor.

36. An apparatus for helically moving an inspection probe within a tube comprising:
  a head assembly insertable in a tube to be inspected for helically moving an inspection probe therein along a longitudinal axis of the tube, said head assembly comprising a first portion fixable to the tube by a fixing means and a second portion movably connected to said first portion by means for helically moving said second portion in response to driven rotary movement of said second portion with respect to the longitudinal axis of the tube, said second portion including means for detachably connecting an inspection probe thereto for helical movement therewith within a tube for inspection thereof; and
  b. a drive frame assembly with drive means slidably mounted thereon, said drive means drivingly connected to said second portion of said head assembly by a conduit means connected between said drive motor and said second portion for imparting the driven rotary movement to said second portion, wherein helical movement of said second portion causes said drive means to move linearly along said drive frame assembly.

* * * * *